United States Patent [19]

Berg et al.

[11] 4,253,934

[45] Mar. 3, 1981

[54] AGING TREATMENT FOR EXHAUST GAS OXYGEN SENSOR

[75] Inventors: Morris Berg, Grand Blanc; Slater W. Hawes, Fenton; Frederick L. Kennard, III, Holly; Paul C. Kikuchi, Flint, all of Mich.

[73] Assignee: General Motors Corporation, Detroit, Mich.

[21] Appl. No.: 30,747

[22] Filed: Apr. 17, 1979

[51] Int. Cl.³ ............................................. G01N 27/58
[52] U.S. Cl. .................................................. 204/195 S
[58] Field of Search ............................ 204/195 S, 1 S

[56] References Cited

U.S. PATENT DOCUMENTS

| | | | |
|---|---|---|---|
| 3,503,809 | 3/1970 | Spacil | 204/195 S X |
| 3,844,920 | 10/1974 | Burgett et al. | 204/195 S |
| 3,935,089 | 1/1976 | Togawa et al. | 204/195 S |
| 3,978,006 | 8/1976 | Topp et al. | 252/477 R |
| 4,021,326 | 5/1977 | Pollner et al. | 204/195 S |
| 4,116,883 | 9/1978 | Rhodes | 252/463 |
| 4,136,000 | 1/1979 | Davis et al. | 204/195 S |
| 4,169,777 | 10/1979 | Young et al. | 204/195 S |
| 4,186,071 | 1/1980 | Romine et al. | 204/195 S |

FOREIGN PATENT DOCUMENTS 1524520  9/1978  United Kingdom .

OTHER PUBLICATIONS

S. Pizzini et al., J. Appl. Electrochemistry, vol. 3, pp. 153–159, (1973).

J. E. Bauerle, J. Phys. Chem. Solids, vol. 30, pp. 2657–2670 (1969).

Y. L. Sandler et al., J. Electrochemical Soc., vol. 112, No. 9, pp. 928–931, (1965).

*Primary Examiner*—G. L. Kaplan
*Attorney, Agent, or Firm*—Robert J. Wallace

[57] ABSTRACT

In a preferred embodiment of the invention, a method of making a solid electrolyte electrochemical-type exhaust gas oxygen sensor. A platinum exhaust electrode is sputtered onto a zirconia body and the body then heated in nitrogen at 700°–900° C. for at least 30 minutes to reduce rich-to-lean switching time response.

3 Claims, No Drawings

AGING TREATMENT FOR EXHAUST GAS OXYGEN SENSOR

FIELD OF THE INVENTION

This invention relates to solid electrolyte exhaust gas oxygen sensor. It more particularly relates to a process of heat treating such sensors to improve their functional properties prior to their operational use.

BACKGROUND OF THE INVENTION

An automotive-type solid electrolyte exhaust gas oxygen sensor is disclosed in U.S. Pat. No 3,844,920 Burgett et al. The sensing element in such a sensor is a tapered thimble of zirconia. The interior and exterior of the thimble have separate porous electrode coatings of platinum or the like. The inner electrode is exposed to a source of oxygen, such as air or mixed oxides for establishing a reference potential. It is generally formed by painting a coating of platinum ink onto the thimble, drying it and then firing the coated thimble. An improved technique for applying the coating is described in United States patent application Ser. No. 3,030,776 (now abandoned), entitled "Reference Electrode Process for Exhaust Gas Oxygen Sensor", prepared for filing in the name of John Trevorrow, and assigned to the assignee of this invention.

The outer electrode is exposed to the exhaust gas for establishing a potential determined by its oxygen concentration. This electrode can be a thick film platinum electrode applied in the same manner as the inner electrode. However, it may be more desirable that it be a thin film electrode, applied by evaporation, sputtering, chemical vapor deposition, or other such thin film deposition techniques. However, it has been difficult to consistently reproduce desirable properties in such thin film electrodes. Apparently, thin film electrodes are produced with varying porosity, surface area, platinum microstructure, and/or electrical properties. In any event, it has been difficult to consistently reproduce the most desirable electrical, electrochemical and catalytic parameters in sensors having thin film exhaust electrodes. As a result, yields of the most desirable sensors have been reduced. Various procedures have evolved to improve electrode, i.e. sensor, performance. For example U.S. Pat. No. 3,978,006 Topp et al asserts that nonporous thin film electrodes can be made porous by a heat treatment. U.S. Pat. No. 4,136,000 Davis et al discloses chemical and electrochemical electrode activation treatments. It is also known that sensor characteristics may improve somewhat during initial periods of use. Hence, sensors have also been functional in representative exhaust gas systems before installation in operational systems, to both stabilize and improve sensor properties.

An improved sputtering process for producing platinum thin films is described and claimed in concurrently filed United States patent application Ser. No. 3,030,775 (now abandoned), entitled "Exhaust Electrode Process for Exhaust Gas Oxygen Sensor", filed in the names of Terry J. Gold and Ralph V. Wilhelm, Jr. and assigned to the assignee hereof. The thin films are porous as deposited and have more consistent electrode characteristics. Hence, sensors with more reproducible characteristics are provided. Lean-to-rich switching response times below 600 milliseconds at 700° F. are consistently obtained without using any electrode or sensor post-electroding treatments. Rich-to-lean switching response times may vary from 250 milliseconds to 1200 milliseconds at 700° F. However, they consistently drop to below 600 milliseconds after functional operation for 0.5-3 hours in exhaust gas. We have now found that sensors having such electrodes need not be functionally operated in exhaust gas to reduce their rich-to-lean switching response times and to stabilize them at this low switching time. We have found that an equivalent effect can be obtained by a simple furnace treatment of the zirconia element after electroding and before its incorporation in a sensor assembly.

OBJECTS AND SUMMARY OF THE INVENTION

An object of this invention is to provide a furnace treatment for improving and stabilizing selected electrical properties in an exhaust gas oxygen sensor having a sputtered thin film exhaust gas electrode. The invention comprehends heat treating a zirconia solid electrolyte element after sputtering a porous thin film platinum exhaust electrode thereon. The heat treatment is in a chemically neutral environment such as substantially pure nitrogen at atmospheric pressures. Strongly reducing atmospheres are to be avoided, since they adversely affect sensor controllability. The heat treatment must not be followed by any significant oxidizing or strongly reducing heat treatment prior to sensor operation.

DESCRIPTION OF THE PREFERRED EMBODIMENT

In this invention, a simple furnace treatment is used to reduce rich-to-lean switching response time of zirconia solid electrolyte sensors having thin film platinum electrodes prepared according to the method described and claimed in the aforementioned United States patent application Ser. No. 3,030,775 (now abandoned). It substantially eliminates the reduction in rich-to-lean response time possibly attendant the first few hours of operational use of such sensors in a closed loop system for maintaining air/fuel ratio stoichiometry in an internal combustion engine. The aforementioned Ser. No. 3,030,775 (now abandoned) discloses sputtering platinum electrodes onto vitrified zirconia bodies. The electrodes are porous as deposited, and exhibit switching response times of about 250-1200 milliseconds without any subsequent electrode treatments. The zirconia bodies are generally heated in air after electroding to increase electrode adhesion. The thin film exhaust electrode is then covered with a porous ceramic coating. Best properties were obtained with such sensors after they functioned electrically for 0.5-3 hours in actual or simulated exhaust gas. We have found how to eliminate the functional treatment. In accordance with this invention the sensor's zirconia sensing element is heated in a chemically neutral environment, as a final heat treatment before sensor assembly and operational use.

The sensing element primarily is a body of zirconia that is partially or fully stabilized in its cubic form, preferably by an addition of about 4-8 mole percent yttria. In a preferred form, the body is a tapered thimble, that is open at one end and closed at the other. The open end has a circumferential flange. In one example the thimble is abut 3-5 cm, preferably about 3.7 cm, long along its axis and has an external taper of about 3 degrees and 38 minutes. Its closed end has a diameter of about 0.4 cm and is rounded. The outer surface on the closed end has a spherical radius of curvature of about 3 mm. Its maximum diameter adjacent the circumferential flange is about 0.82 cm. The inner electrode is applied first. After it is dried and fired to the zirconia surface, the outer electrode is applied. If desired, a stripe of a platinum cermet or the like can be applied and fired to the zirconia outer surface before sputtering the outer electrode onto it, to increase sensor durability.

The zirconia outer surface can then be prepared to receive the sputtered outer electrode coating by ultrasonically cleaning it in a degreaser using a freon-based solvent. The thimble is then heated in air at about 600° C. for one hour. It is then placed on a horizontal flat sputtering anode in a vacuum chamber. The thimble is vertically positioned with its open end down and its closed end spaced about 3.8 cm below a platinum sputtering target. A platinum sheet is bonded to a supporting copper backing plate that together forms a sputtering target. The target is assembled with a cathode that includes a water cooling means and a magnet array. Hundred of thimbles can thus be simultaneously coated during one sputtering cycle. An argon atmosphere of a pressure of about 10–20 millitorr is established in the vacuum chamber. A DC voltage of about 500–800 volts is applied between the anode and target to establish a plasma, and DC power is adjusted to about 13–22 watts/$cm^2$ of target area. Sputtering is continued under these conditions for about 3–5 minutes. No special means are used in the pallet, pallet carrier or anode to cool the thimbles during sputtering. A preferred coating is 1.0 micrometer thick or more on the rounded end of the thimble, about 0.75–1.0 micrometer thick about 0.5 cm back from that end, and about 0.3–0.75 micrometer thick about 2 cm back from that end.

We prefer to heat the zirconia thimble after the outer platinum electrode has been sputtered onto it, to increase electrode adhesion to the zirconia. Adhesion can be increased by heating the electroded thimble in air for about one hour at 800° C. Higher temperature treatments can be used but tend to open large pores in the coating. Extremely high temperature treatments sinter the coating causing it to form unconnected platinum islands. As-formed apparent surface area can decrease significantly even during the 800° C. treatment. However, so long as the coating had a high surface area as deposited, the reduction in apparent surface area does not seem detrimental to sensor performance.

Then, we prefer to apply a porous ceramic coating onto the outer platinum electrode, leaving a portion of the electrode film uncovered for making a low resistance electrical connection to the electrode. The porous ceramic coating can be a hydrasol such as disclosed in U.S. Pat. No. 4,116,883 Rhodes. However, we prefer it to be flame sprayed magnesium aluminate spinel. The thus coated zirconia thimbles are then heated in substantially pure nitrogen for one or more periods of 0.5–1.5 hours at about 800° C. and then incorporated into sensor assemblies. Sensor rich-to-lean switching time response will be reduced by the nitrogen heat treatment. In many instances, one such treatment will reduce it so much that it will not reduce significantly further when the sensor is operationally used. No chemical or electrolytic activation of electrodes is needed. Representative samples from one batch of so electroded thimbles exhibited as as-formed rich-to-lean transition time having a mean value of 977 milliseconds, with a standard deviation of 292 milliseconds and a controllability having a mean value of 0.22 air/fuel ratios on the lean side of stoichiometry, with a standard deviation of 0.04 air/fuel ratios. A group of 50 elements from this batch were treated in a production-type furnace at 800° C. for 40 minutes, with the furnace atmosphere being substantially pure nitrogen. A first lot from this group had a mean rich-to-lean transition time of 202 milliseconds, with a 46 millisecond standard deviation. A second lot from this group had a mean rich-to-lean transition time of 176 milliseconds, with a standard deviation of 37 milliseconds. The controllability of both the first and second sensor lots had a mean value of 0.05 air/fuel ratios, with a standard deviation of 0.02 air/fuel ratios. Even better results were obtained when another group of sensors from this same batch was heated at 800° C. for one hour in a laboratory muffle furnace under substantially pure nitrogen. This latter group had a mean rich-to-lean transition time of approximately 89 milliseconds, with a standard deviation of 26 milliseconds. Analogously the controllability of this latter group of sensors was 0.04 air/fuel ratios on the lean side of stoichiometry, with a standard deviation of 0.01 air/fuel ratios. All transition times were measured at 700° F.

It appears that the advantages of this invention are obtained only if the treatment atmosphere is substantially devoid of oxygen. A nitrogen atmosphere at atmospheric pressure should not contain more than 0.1% by volume oxygen and preferably less than 0.01% by volume. On the other hand, the atmosphere should not be reducing in character, as this tends to shift sensor controllability to the rich side of stoichiometry. In current systems, it is undesirable.

The duration of treatment in accordance with the invention can vary, depending upon several factors, including the degree of reduction in rich-to-lean switching response time that is desired. Generally, exposure to pure nitrogen for 30 minutes at atmospheric pressure and at 800° C. seems necessary to obtain any significant benefits. In many instances, treatments of about 0.75 hour appear to be adequate. However, if the electrode quality is not as high, 90 minutes may be required. In any event, we prefer to employ a fixed time of treatment, and to simply repeat the treatment as many times as necessary to obtain the desired reduction.

We prefer atmospheric pressure for simplicity but recognize treatments at other pressures would probably be useful too. Analogously, we prefer treatment at about 800° C. Above this temperature, particularly above about 900° C., large openings form in the as-sputtered film and apparent surface area drops. We believe this to be objectionable, especially if it produces isolated platinum islands. At temperatures below about 700° C., it takes too long to get the improvement.

The embodiments of the invention in which an exclusive property or privilege is claimed are defined as follows:

1. In a method of making a sensing element for a solid electrolyte electrochemical exhaust gas oxygen sensor that includes sputtering a porous platinum thin film electrode onto a zirconia body and applying a protective overcoat onto the electrode, the improvement wherein the zirconia body is subsequently heated to a temperature of about 700°–900° C. for at least about 0.5 hours in a substantially pure nitrogen atmosphere without concurrent electrical treatment as a final heat treatment before exposure to exhaust gases and said heat treatment is effective to reduce rich-to-lean switching response time.

2. In a method of making an exhaust gas electrode on a sensing element for a solid electrolyte electrochemical exhaust gas oxygen sensor that includes sputtering a porous platinum thin film electrode onto a zirconia body by means of an inert gas discharge, heating the body to a temperature of about 700°–900° C. after sputtering, and then spraying a porous spinel coating at a high temperature onto at least principally active portions of the electrode, the improvement wherein the zirconia body is subsequently heated to a temperature of about 700°–900° C. in a nitrogen atmosphere having not more than about 0.1% by volume oxygen for at least one period of about 0.5–1.5 hours without concurrent electrical treatment and the subsequent heating is effective to so significantly reduce rich-to-lean switching response time that it does not substantially decrease further upon initial operation of said element in said sensor.

3. In a method of making an exhaust gas electrode on a sensing element for a solid electrolyte electrochemical exhaust gas oxygen sensor that includes sputtering a porous platinum thin film electrode onto a zirconia body by means of an argon discharge at a DC power of about 13–22 watts/cm$^2$ of target area, heating the body in air to a temperature of about 700°–900° C. after sputtering, and then flame spraying a porous spinel coating onto at least principally active portions of the electrode, the improvement wherein after the flame spraying, the zirconia body is heated to a temperature of about 700°–900° C. in a nitrogen atmosphere having less than about 0.01% by volume oxygen for at least one period of about 0.5–1.5 hours without concurrent electrical treatment and the heating is effective to reduce rich-to-lean switching response time to below about 250 milliseconds without adversely affecting sensor controllability, and switching response time does not substantially decrease further upon initial operation of said element in said sensor.

* * * * *